United States Patent [19]

Buess et al.

[11] Patent Number: 4,858,595
[45] Date of Patent: Aug. 22, 1989

[54] MEDIASTINOSCOPE

[76] Inventors: Gerhard Buess, Berliner Strasse 1, 6501 Niederolm; Manfred Boebel, Allmandstrasse 18, 7136 Oetisheim; Siegfried Hiltebrandt, August-Lämmle-Strasse 16, 7134 Knittlingen, all of Fed. Rep. of Germany

[21] Appl. No.: 254,109

[22] Filed: Oct. 6, 1988

[30] Foreign Application Priority Data

Dec. 18, 1987 [DE] Fed. Rep. of Germany ....... 3743042

[51] Int. Cl.⁴ .............................................. A61B 1/00
[52] U.S. Cl. ...................................................... 128/6
[58] Field of Search ...................... 128/3, 4, 5, 6, 7, 8

[56] References Cited

U.S. PATENT DOCUMENTS

| | | | |
|---|---|---|---|
| 1,606,861 | 11/1926 | Wolf | 128/8 |
| 2,243,285 | 5/1941 | Pope | 128/6 |
| 4,606,330 | 8/1986 | Bonnet | 128/7 |

*Primary Examiner*—William H. Grieb
*Attorney, Agent, or Firm*—Hill, Van Santen, Steadman & Simpson

[57] ABSTRACT

A mediastinoscope having a shaft which is traversed by a photoconductor and an observation optical system, with the shaft being provided at its distal end with an atraumatically shaped cap, the greatest diameter of which is greater in comparison with the diameter of the shaft and into a cavity of which distally has an aperture, channels and the end of the optical system open out. Auxiliary instruments extending through a shaft channel can be conducted distalwards as far as the treatment location.

7 Claims, 1 Drawing Sheet

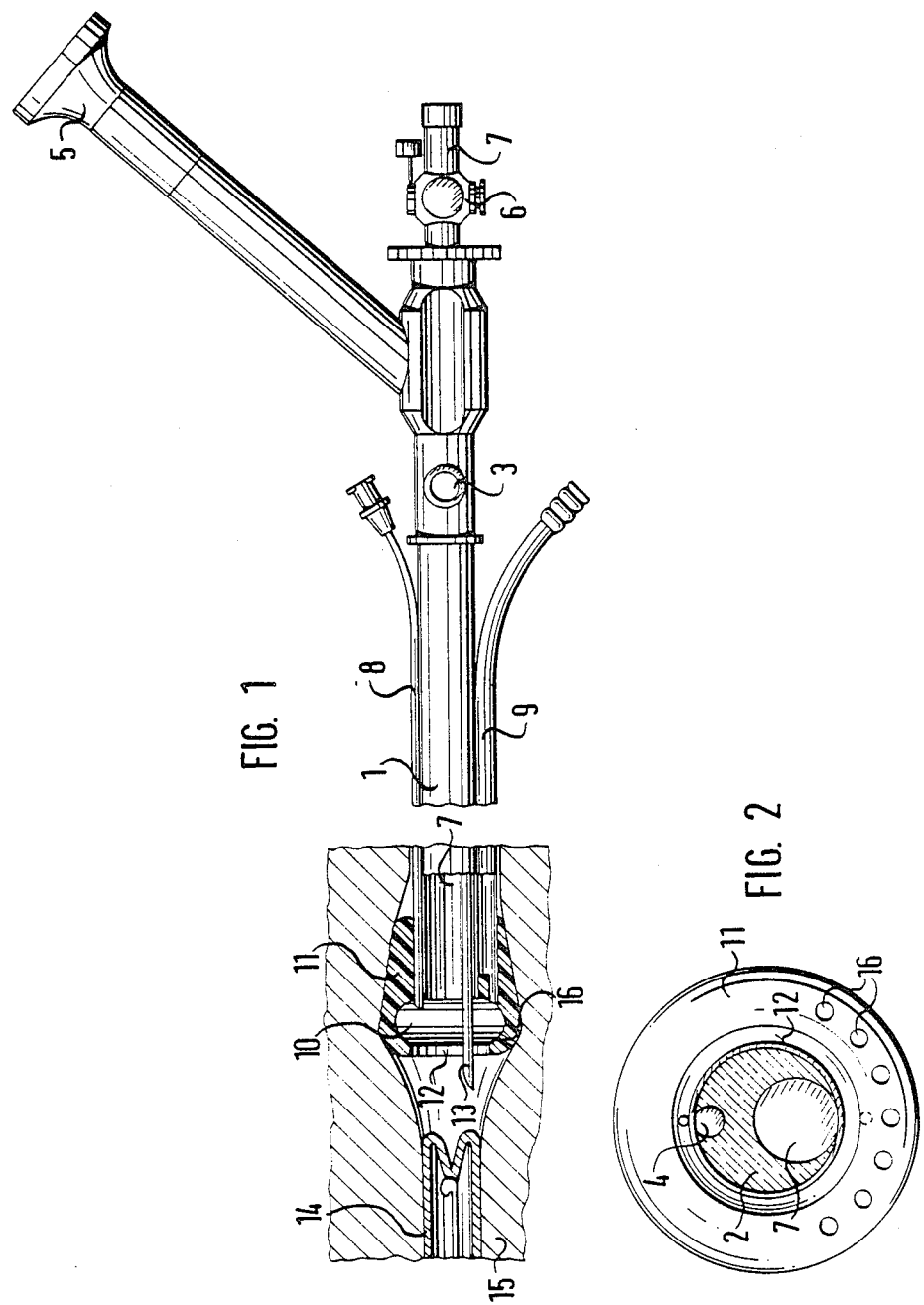

MEDIASTINOSCOPE

BACKGROUND OF THE INVENTION (a) Field of the Invention

This invention relates to a mediastinoscope having a shaft which is traversed by a photoconductor and an observation optical system.

(b) Description of the Prior Art

Mediastinoscopes are known which have a shaft traversed by an observation optical system.

The principle of the surgical treatment of aesophageal carcinoma consists in the extensive surgical removal of the aesophagus and the replacement of the organ by a hoisted part of the stomach or interpolation of an intestine part.

An exact removal of the aesophagus can be effected only by a simultaneous opening of the pleural cavity and of the abdominal cavity. However, this leads to an extreme burdening of the patient and to an increased risk. Frequently, therefore, nowadays the removal of the aesophagus by way of an opening of the pleural cavity is dispensed with and instead an obtuse dissection is undertaken.

For this purpose, on the left-hand side of the neck above the clavicle an incision is undertaken and through this the aesophagus is severed surgically both at its cervical end and, after opening of the abdominal cavity has been effected, in the region of the cardia. Then, through the opened abdomen and the detached aesophagus a probe or respectively an auxiliary instrument is conducted as far as the upper detached partially free-dissected and inwardly turned-over end and is connected to this. Simultaneously with the free-dissecting of the aesophagus in the direction of the abdomen by means of a finger the aesophagus is drawn into the abdominal cavity. Since, the case of this mode of procedure, the aesophagus cannot be completely detached from the surrounding mediastinum, it is necessary to tear the residual length off.

After removal of the aesophagus from the opened abdomen has been effected, this can be replaced by an interponate. This type of removal of aesophaguses is bound up with considerable risk for the patient, since inter alia haemorrhages occurring upon the blind free-dissection of the aesophagus cannot be immediately discerned and coagulated.

The main object of the present invention consists in being able to perform free-dissection of the aesophagus from the surrounding tissue under direct observation, being able to stanch at once possible occurring haemorrhages and being able to remove accumulations of body secretions such as blood and the like in a deliberate manner.

SUMMARY OF THE INVENTION

To this end, the present invention consists in a mediastinoscope having a shaft which is traversed by a photoconductor and an observation optical system, characterised in that the shaft is provided at the distal end with an atraumatically shaped cap, the greatest diameter of which is greater as compared with that of the shaft and into the cavity thereof which has distally an aperture there open channels and the end of the optical system, and in that auxiliary instruments extending through a shaft channel can be guided distalwards as far as the treatment spot.

Preferably the shaft channel having a sealing cap at the proximal side, for the passing through of the auxiliary instruments can be shut off at the proximal end.

In a preferred embodiment, the observation optical system may be angled laterally proximally to the ocular. Preferably, the distal-side part of the cap has, on the one circumferential side, channels which lie opposite to the mouth of a suction and flushing channel.

As a result of this solution it is possible, after performing the cut on the left-hand side of the neck and after severing and free-dissecting of the aesophagus in the region of its cervical end has been effected, to introduce the mediastinoscope in order to be able to perform the further separation of the aesophagus from the surrounding tissue with simultaneous abdomenwards extraction under visual control. Furthermore, it is possible to suck off accumulations of fluids and to coagulate possibly occurring haemorrhages by means of an auxiliary instrument introduced through the instrument channel of the mediastinoscope into the body cavity.

BRIEF DESCRIPTION OF THE DRAWINGS

In order that the invention may be more readily understood, an embodiment thereof will now be described, by way of example, with reference to the accompanying drawings in which:

FIG. 1 is a part-longitudinal sectional side elevation of a mediastinoscope with the longitudinal section being through the distal length part being used, and FIG. 2 is a distal front view of the mediastinoscope of FIG. 1, to an enlarged scale.

DESCRIPTION OF THE PREFERRED EMBODIMENT

Referring to the drawings, the mediastinoscope illustrated comprises a shaft 1 through which at least one photoconductor 2 having a proximal connecting socket 3, an optical system 4 having an ocular 5 arranged obliquely to the longitudinal axis of the instrument and a channel 7, which can be shut off proximally at 6, for auxiliary instruments that are to be conducted through the shaft 1, such as cutting and coagulation instruments or the like, extend.

Beside the shaft 1 there extends a channel 8, which is angled in front of the distal terminal window of the optical system or is provided with a nozzle, so that the window can be rinsed free for the unrestricted observation in case of need.

Furthermore, a suction and flushing channel 9 extends along the shaft 1, in order to be able to suck of quantities of fluid, such as blood, flushing fluids or the like, which have accumulated in the operation region.

The photoconductors 2, the optical system 4 and the channel 7 for the auxiliary instruments end distally with the termination of the shaft 1. The channels 8 and 9 open into the cavity 10 of an atraumatically designed cap 11 which is non-detachably secured to the distal end of the shaft 1, which advantageously consists of a plastics or other suitable synthetic material and the greatest diameter of which is greater than that of the shaft 1. This cap 11 is provided at the distal side with an aperture 12, the diameter of which corresponds approximately to the diameter of the shaft 1 and through which the distal end of an auxiliary instrument 13 can be passed, in order to release the aesophagus 14 from the tissue 15 which has coalesced therewith. As a result of the design, in accordance with the invention, of the mediastinoscope it is possible along with simultaneous swivelling and rotation to a limited degree to apply the auxiliary instrument 13, e.g. a cutting and coagulation instrument, between aesophagus 14 and the tissue 15 surrounding this and to perform the free-dissection.

The handling of the mediastinoscope is as follows: After a left-side neck cut above the clavicle the aesophagus is severed at its cervical end. With the mediastinoscope then the aesophagus is rid on the left-hand side of its connections to the mediastinum. In this respect the blood vessels are, prior to the severing, coagulated or closed by a clip. The lymphatic glands are so dissected that the lymphatic discharge paths can be removed as far as possible together with the aesophagus in one dissection. If, as a result of the dissection the aesophagus is exposed in its entire length, from the abdominal cavity a probe is conducted to the tip of the mediastinoscope and this probe is grasped with an instrument and conducted up through the mediastinum to the neck. By pulling from the abdominal cavity on the probe, the aesophagus is then turned over. With gradual lowering of the aesophagus then the vessels tighten against the side which is not yet freely dissected and can now be taken care of with the mediastinoscope in the manner which has already been described.

Since, as a result of the free-dissection, the rotating and the swivelling of the distal mediastinoscope end within a restricted region, the distal terminal window of the optical system can get dirty through emerging blood or other body secretions and can thus restrict the view for the operator, a rinsing-free of the distal optical-system viewing window by means of a flushing liquid which can be supplied through the channel 8 is possible. By way of the channel 9, the space in front of the distal end of the mediastinoscope is rid of blood, secretions and the like. Through the channels 9,16 and the cavity 10 in the distal termination part of the cap 11 it is also possible to introduce a flushing liquid into the body cavity, in order in this way to be able to undertake a deliberate flushing. In order, during the free-dissection and the extraction of the aesophagus, to be able to stanch occurring haemorrhages, it is possible to conduct a coagulation probe or respectively the cutting and coagulation instrument through the channel 7 up to the relevant tissue location.

As a result of the invention it is thus for the first time possible to be able to remove the aesophagus completely under direct visual control without opening the pleural cavity and to be able deliberately to coagulate any haemorrhages which occur and if necessary to be able to supply rinsing liquids or carry off body secretions.

In further development of the mediastinoscope in accordance with the invention, it is advantageous to integrate the channels 8,9 arranged on the shaft 1 actually in the shaft in order thereby to facilitate the cleaning and sterilisation.

Furthermore, it is possible to arrange the optical system displaceably inside the outer shaft, in order thereby to be able to conduct the distal optical-system viewing window closer up to the location of the endoscopic intervention or remove same from this. For this purpose the outer shaft, which has to have an appropriate seal at its proximal end, can have a handle, in order thereby to facilitate the manipulation in the body cavity.

It should be appreciated that the invention is not limited to the embodiment described but includes all modifications and variations falling within its scope.

What is claimed is:

1. A mediastinoscope having a shaft which is traversed by a photoconductor and an observation optical system, said shaft having a distal end provided with an atraumatically shaped cap having a greatest diameter which is greater than that of the shaft and defining a cavity with a distal aperture, into which said cavity there open channels and the end of the optical system, said shaft defining a shaft channel through which auxiliary instruments extending therethrough can be guided distalwards as far as a treatment location.

2. A mediastinoscope according to claim 1 in which the shaft channel having a sealing cap at the proximal side, for the passing through of the auxiliary instruments can be shut off at the proximal end.

3. A mediastinoscope according to claim 1, in which the observation optical system is angled laterally proximally with respect to an occular.

4. A mediastinoscope according to claim 2, in which the observation optical system is angled laterally proximally with respect to an occular.

5. A mediastinoscope according to claim 1, in which a distal-side part of the cap has, on a one circumferential side, channels which lie opposite to a mouth of a suction and flushing channel.

6. A mediastinoscope according to claim 2, in which a distal-side part of the cap has, on a one circumferential side, channels which lie opposite to a mouth of a suction and flushing channel.

7. A mediastinoscope according to claim 3, in which a distal-side part of the cap has, on a one circumferential side, channels which lie opposite to a mouth of a suction and flushing channel.

* * * * *